United States Patent
Cominsky

(10) Patent No.: US 6,664,434 B2
(45) Date of Patent: Dec. 16, 2003

(54) MEDICAL DEVICE FOR CONTAINING BODY FLUIDS

(76) Inventor: John C. Cominsky, 259 N. Hwy. 161, Clover, SC (US) 29710

( * ) Notice: Subject to any disclaimer, the term of this patent is extended or adjusted under 35 U.S.C. 154(b) by 15 days.

(21) Appl. No.: 09/576,692

(22) Filed: May 23, 2000

(65) Prior Publication Data

US 2003/0163071 A1 Aug. 28, 2003

(51) Int. Cl.$^7$ ................................................. A61F 13/00
(52) U.S. Cl. ........................... 602/41; 602/61; 602/74; 602/79; 128/888
(58) Field of Search ................................. 602/3, 41, 42, 602/79, 43, 60, 63; 2/22; 128/882, 888

(56) References Cited

U.S. PATENT DOCUMENTS

| | | | |
|---|---|---|---|
| 2,926,665 A | 3/1960 | Seese | |
| 4,205,674 A | 6/1980 | Porat et al. | |
| 4,269,181 A | 5/1981 | Delannoy | |
| 4,616,644 A | * 10/1986 | Saferstein et al. | 602/43 |
| 5,086,763 A | * 2/1992 | Hathman | 602/42 |
| 5,115,801 A | 5/1992 | Cartmell et al. | |
| 5,328,449 A | 7/1994 | Andrews et al. | |
| 5,437,621 A | 8/1995 | Andrews et al. | |
| 5,480,377 A | 1/1996 | Cartmell et al. | |
| 5,538,500 A | 7/1996 | Peterson | |
| 5,592,953 A | * 1/1997 | Delao | 128/882 |
| 5,609,569 A | 3/1997 | Offenhartz | |
| 5,637,080 A | * 6/1997 | Geng | 602/58 |
| 5,762,620 A | 6/1998 | Cartmell et al. | |
| 5,823,977 A | * 10/1998 | Dalyea | 602/3 |
| 5,875,493 A | * 3/1999 | MacDonald | 2/172 |
| 5,899,871 A | 5/1999 | Cartmell et al. | |

* cited by examiner

*Primary Examiner*—Kim M. Lewis
(74) *Attorney, Agent, or Firm*—Christopher C. Dremann

(57) ABSTRACT

A medical device for containing body fluids includes an elongate sleeve and at least one closure strap. The elongate sleeve defines a longitudinal axis and has at least one open end. The sleeve is made of a material that has an absorbent layer and a substantially transparent, nonporous layer positioned outwardly of the absorbent layer. Preferably, the material of the sleeve also includes a non-adherent, porous layer positioned inwardly of the absorbent layer. The strap is attached to the sleeve for closing the open end and for positioning and securing the sleeve over a wounded area or over a dressing covering a wound. The strap is made of a flexible, elastic material. The strap is wrapped completely around the sleeve and is affixed to itself, thus positioning and securing the sleeve over the wounded area or the dressing. In one preferred embodiment, the medical device includes an elongate sleeve having a pair of open ends and a pair of straps. In another preferred embodiment, the medical device includes an elongate sleeve having one open end, one closed end and a single strap. The sleeve is cut at an angle relative to the longitudinal axis defined by the sleeve to form the open end.

11 Claims, 3 Drawing Sheets

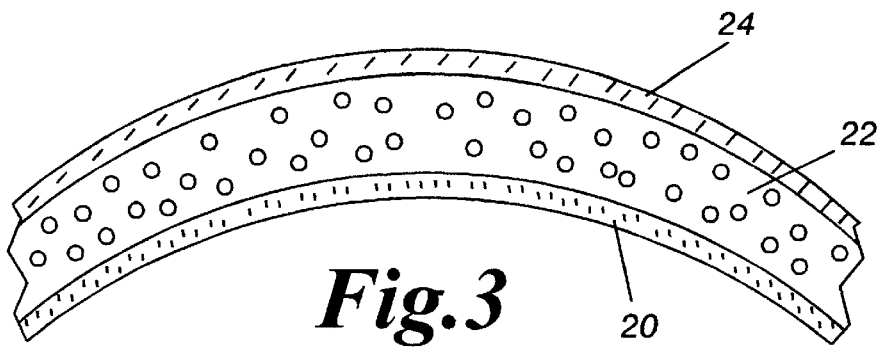
Fig.3
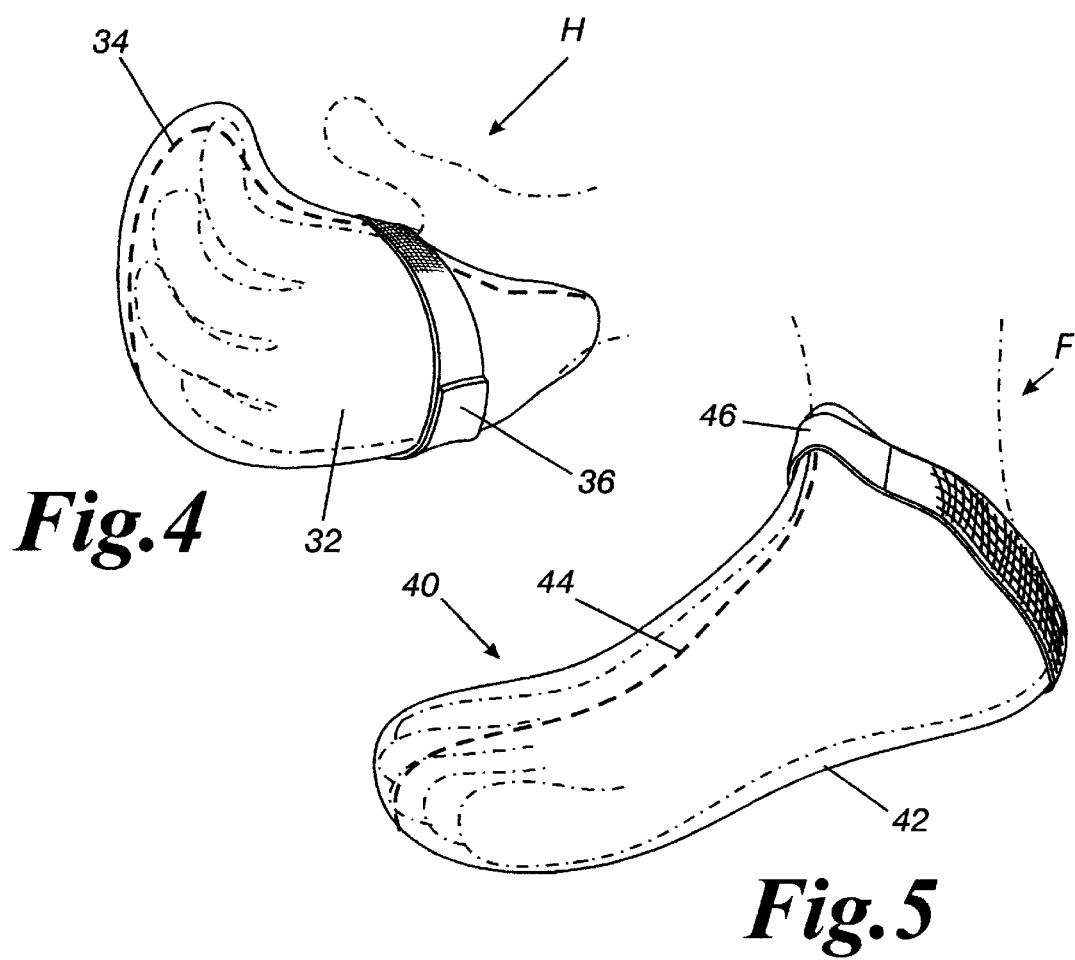
Fig.4
Fig.5

MEDICAL DEVICE FOR CONTAINING BODY FLUIDS

CROSS REFERENCE TO RELATED APPLICATION (none)

FIELD OF THE INVENTION

This invention relates generally to a medical device for containing body fluids. More particularly, the invention is a pre-formed, first response type medical device for containing blood and other body fluids in an emergency until medical assistance is available or while the victim is being transported to a medical facility.

BACKGROUND OF THE INVENTION

In emergency situations in which people are wounded, it is imperative to protect open wounds from further injury and the environment. It is also important to protect rescue workers and medical personnel from the body fluids of the victim because the victim may be infected with any of a number of communicable diseases that are transmitted through blood and other body fluids. Thus, it is apparent that there is a need for an improved medical device that protects open wounds from further injury and the environment. It is further apparent that there is a need for an improved medical device that contains blood and other body fluids, thereby protecting rescue and medical personnel from communicable diseases borne by the body fluids of the victim.

In multiple victim incidents such as airplane crashes, industrial accidents and natural disasters, rescuers and medical personnel need to move quickly from patient to patient assessing injuries and providing emergency first aid. As a result, wounds are covered by any available dressing, such as towels, bandages, gauze or sheets of thin plastic material. The dressing may not absorb blood and other body fluids, and thus, may not protect rescue and medical personnel from exposure to the blood and other body fluids of the victim. While these dressings typically reduce or stop bleeding and protect the wound from further injury and the environment, they are often cumbersome and difficult to position and secure over the wound. In addition, they are generally not available in different sizes to fit over various body parts. Thus, it is apparent that there is a need for an improved medical device that is easily positioned and secured over a wounded area or over a dressing covering a wound. It is further apparent that there is a need for an improved medical device that is available in different sizes.

Because many conventional dressings are not impervious to liquids, the wound may come into contact with liquids, such as water, oil or fuel, at the accident scene, thereby subjecting the wound to possible infection. Additionally, the extent of continued bleeding cannot be observed without removing the dressing from the wound, thereby potentially causing bleeding to resume and exposing the wound to further injury or infection. Thus, it is apparent that there is a need for an improved medical device that is impervious to liquids. It is further apparent that there is a need for an improved medical device that allows the extent of continued bleeding to be observed without removing the medical device.

It is quite common that blood and other body fluids will continue to be excreted while wounds from accidents or surgery are healing. Currently, bandages and other tight fitting dressings are applied directly to the wound during the healing process. However, these types of dressings do not adequately contain the blood and other body fluids excreted from the wound. Thus, it apparent that there is a need for a medical device that contains the body fluids that are excreted from the wound during the healing process, thereby preventing the blood and other body fluids from coming into contact with the surrounding environment, such as bedding, clothing and furniture.

SUMMARY OF THE OBJECTS OF THE INVENTION

It is a primary object of the invention to provide a medical device that protects open wounds from further injury and the environment.

It is a further object of the invention to provide a medical device that contains blood and other body fluids, thereby protecting rescue and medical personnel from exposure to the victim's blood and other body fluids.

It is a further object of the invention to provide a medical device that is easily positioned and secured over a wounded area or over a dressing covering a wound.

It is a further object of the invention to provide a medical device that may be produced in different sizes to fit over various body parts.

It is a further object of the invention to provide a medical device that is impervious to liquids.

It is a further object of the invention to provide a medical device that allows the extent of continued bleeding to be observed without removing the medical device.

It is a further object of the invention to provide a medical device that contains the body fluids that are excreted from a wound during the healing process, thereby preventing the blood and other body fluids from coming into contact with the surrounding environment.

SUMMARY OF THE INVENTION

The above objects and others are achieved by a medical device constructed in accordance with the present invention. An improved pre-formed, first response type medical device for containing body fluids includes an elongate sleeve and at least one closure strap. The elongate sleeve defines a longitudinal axis and has at least one open end. The sleeve may be cut at an angle relative to the longitudinal axis defined by the sleeve to form the open end. The sleeve is made of a material that has an absorbent layer and a substantially transparent, nonporous layer positioned outwardly of the absorbent layer. The absorbent layer of the sleeve may be impregnated with an antibacterial agent to prevent infection of the wounded area. Preferably, the material of the sleeve further includes a non-adherent, porous layer positioned inwardly of the absorbent layer. The non-adherent, porous layer likewise may be impregnated with an antibacterial agent to prevent infection of the wounded area. The strap is attached to the sleeve for closing the open end and for positioning and securing the sleeve over the wounded area or over a dressing covering the wound. The strap is made of a flexible, elastic material. The strap is wrapped completely around the sleeve and is affixed to itself, thus positioning and securing the sleeve over the wounded area or over the dressing covering the wound.

In one preferred embodiment, the medical device includes an elongate sleeve and a pair of closure straps. The sleeve defines a longitudinal axis and has a pair of open ends. The sleeve is made of a material having an absorbent layer, a substantially transparent, nonporous layer positioned outwardly of the absorbent layer and a non-adherent, porous layer positioned inwardly of the absorbent layer. The straps are attached to the sleeve for closing the pair of open ends and for positioning and securing the sleeve over the wounded area or over the dressing covering the wound. In this preferred embodiment, the medical device may be used to cover a wounded area or a dressing on a limb, and in particular on the arm or leg, of a victim.

In another preferred embodiment, the medical device includes an elongate sleeve and a single closure strap. The sleeve defines a longitudinal axis and has one open end and one closed end. The sleeve is made of a material having an absorbent layer, a substantially transparent, nonporous layer positioned outwardly of the absorbent layer and a non-adherent, porous layer positioned inwardly of the absorbent layer. The strap is attached to the sleeve for closing the open end and for positioning and securing the sleeve over the wounded area or over the dressing covering the wound. The sleeve is cut at an angle relative to the longitudinal axis defined by the sleeve to form the open end. In this preferred embodiment, the medical device may be used to cover a wounded area or a dressing on an appendage, and in particular on the hand, foot or head, of a victim.

BRIEF DESCRIPTION OF THE DRAWINGS

In view of the aforementioned objects and others, which will become more readily apparent as the nature of the invention is better understood, the present invention consists in the novel combination and arrangement of parts hereinafter more fully described, illustrated and claimed with reference being made to the accompanying drawings in which:

FIG. 3 is an enlarged, partial sectional view of the medical device of FIG. 1 taken along line 3—3 in FIG. 2 illustrating the preferred material of the dressing;

FIG. 4 is an environmental view of an alternative preferred embodiment of a medical device according to the invention positioned and secured over a wounded area or a dressing on the hand of a victim, with the hand of the victim depicted by phantom lines;

FIG. 5 is an environmental view of an alternative preferred embodiment of a medical device according to the invention positioned and secured over a wounded area or a dressing on the foot of a victim, with the foot of the victim depicted by phantom lines;

DETAILED DESCRIPTION OF THE PREFERRED EMBODIMENTS

Figure 1:
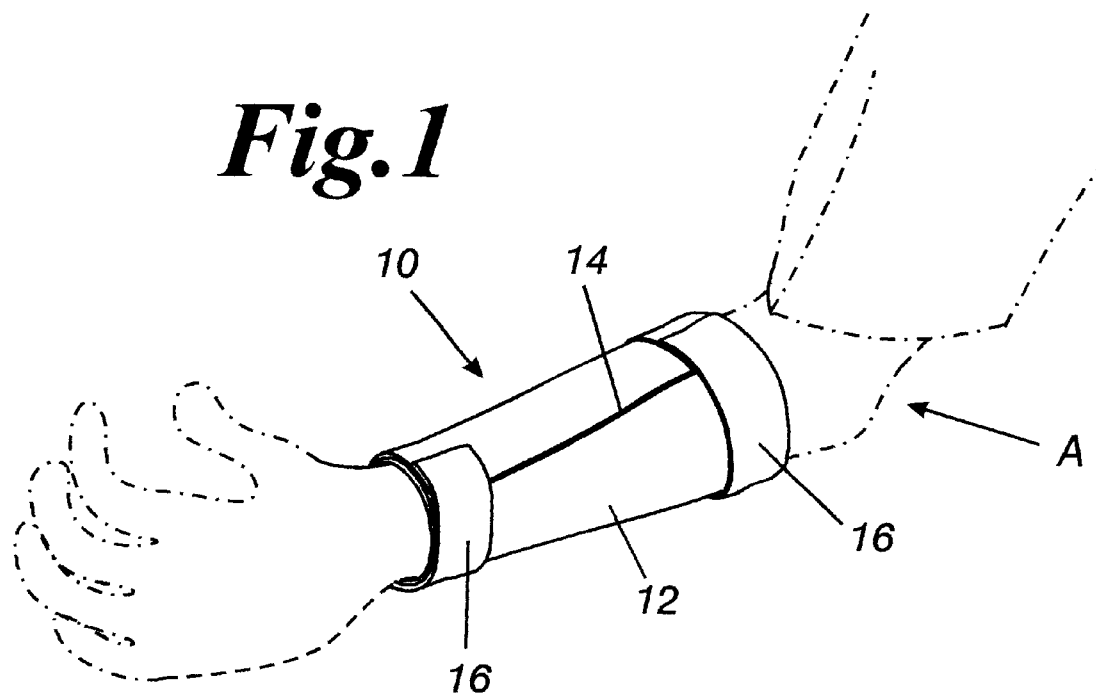
FIG. 1 is an environmental view of a preferred embodiment of a medical device according to the invention positioned and secured over a wounded area or a dressing on the arm of a victim, with the arm of the victim depicted by phantom lines.

A number of preferred embodiments of the present invention will be described more fully hereinafter. However, the invention should not be construed as being limited to the embodiments described herein. Rather, it is intended that the invention be construed broadly to encompass any and all embodiments of a medical device having the features disclosed herein, or equivalents thereof, which is within the skill of an ordinary person in the relevant art. In the description, like reference numerals designate like or corresponding parts throughout the several figures. It is to be also understood that such terms as "longitudinal," "inner," "middle," "outer," "inwardly" and "outwardly" are used in the description for purposes of locating one element of the invention relative to another and are not to be construed as limiting terms. Finally, it should be understood that the illustrations provided in the accompanying figures are for the purpose of describing the various embodiments of the invention, and thus, are not intended to limit the scope of the invention in any manner.

The present invention is a pre-formed medical device for covering a wounded area or a dressing covering a wound, and thereby contain blood and other body fluids. Preferably, the medical device is a "first response" type medical device that fits loosely over a wounded area or a dressing on a limb or appendage of an accident or trauma victim. First response type medical devices are often utilized in multiple victim incidents such as airplane crashes, industrial accidents and natural disasters, where rescuers and medical personnel need to move quickly from patient to patient assessing injuries and providing emergency first aid. Naturally, it is desirable that the medical device protect the wound from further injury and the environment while at the same time protecting rescue and medical personnel from exposure to the communicable diseases that may be borne by the blood and other body fluids of the victim. It is further desirable that the medical device be easy to position and secure over the wounded area or over the dressing. It is further desirable that the medical device be available in different sizes to fit over various body parts. It is further desirable that the medical device be impervious to liquids. It is further desirable that the medical device permit rescue and medical personnel to observe the extent of continued bleeding from the wound without removing the medical device. It is further desirable that the medical device contain the body fluids that are excreted from the wound during the healing process, thereby preventing the blood and other body fluids from coming into contact with the surrounding environment. As will be described and illustrated in greater detail hereinafter, the present invention provides a first response type medical device that satisfies each of the above mentioned concerns.

Figure 2:
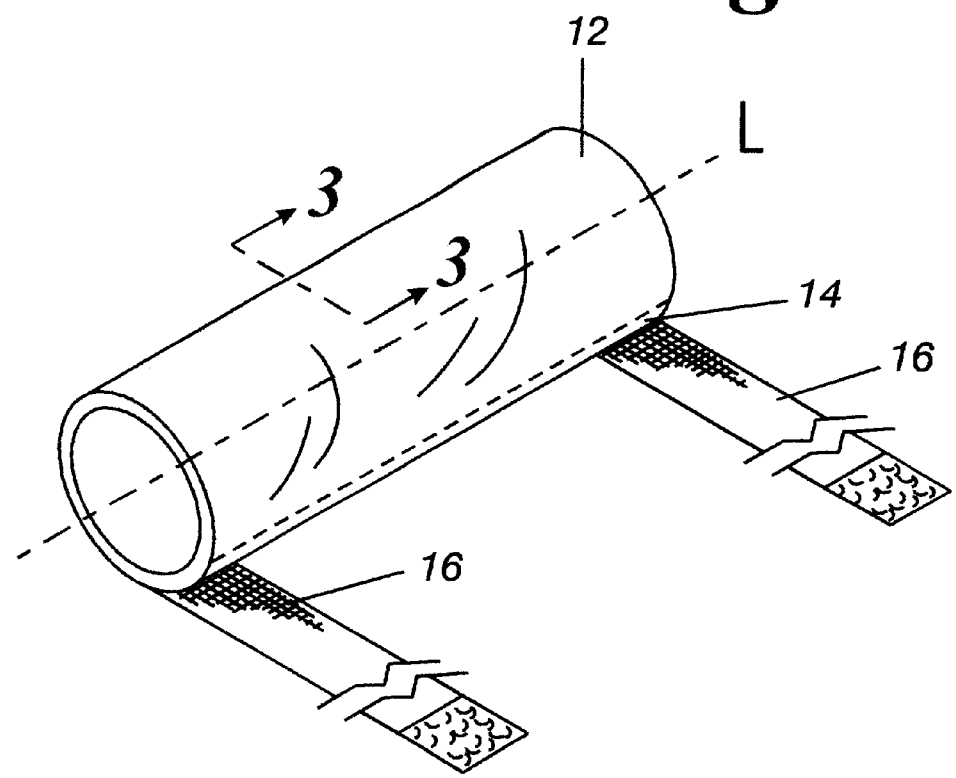
FIG. 2 is a perspective view of the medical device of FIG. 1.

Referring now more specifically to the drawings, FIG. 1 is an environmental view of a preferred embodiment of a medical device 10 according to the invention. In the preferred embodiment shown in FIGS. 1–3, the medical device 10 comprises an elongate sleeve 12 defining a longitudinal axis L (FIG. 2). The sleeve 12 is loose fitting and open at both ends so that the medical device 10 can be easily positioned and secured over a wounded area or a dressing on a victim's limb, and in particular, on a victim's arm or leg. As illustrated in FIG. 1, the preferred embodiment of the medical device 10 shown in FIGS. 1–3 is positioned and secured over a wounded area or a dressing on the arm A of a victim. The sleeve 12 is formed by folding a generally rectangular piece of material so that the lengthwise edges of the material meet. The edges of the material are then joined together along a seam 14 to form the sleeve 12. The edges may be sewn, glued or fastened by any other conventional means to form seam 14. Preferably, however, the seam 14 is heat, ultrasound, or radio frequency (RF) sealed so that the seam 14 is impervious to liquids. Accordingly, the seam 14 prevents the passage of liquids, such as water, oil or fuel, from the surrounding environment to the wound through the seam 14 of the medical device 10. At the same time, the seam 14 prevents the passage of blood and other body fluids from the wound to the surrounding environment through the seam 14 of the medical device 10.

The medical device 10 is positioned and secured over the wounded area or the dressing by at least one closure strap 16 attached to the sleeve 12 of the medical device 10. In the preferred embodiment shown in FIGS. 1–3, a pair of straps 16 are provided adjacent the opposed, open ends of the medical device 10. The straps 16 are wrapped around the open ends of the sleeve 12, thus closing the ends of the sleeve 12 with the wounded area or the dressing completely covered by the medical device 10. The straps 16 may also be used to apply sufficient pressure to the wound so that rescue and medical personnel are not required to continually press the medical device 10 against the wound during the rescue attempt or while the victim is being transported to a medical facility. The straps 16 may be sewn, glued, or fastened by any other conventional means to the sleeve 12 of the medical device 10. For optimum strength and ease of manufacture, the straps 16 are preferably sewn into one of the edges of the material of the sleeve 12 and heat, ultrasound or RF sealed along with the edges of the material of the sleeve 12 as the seam 14 is formed.

Preferably, the straps 16 are made of a flexible, elastic material that is wrapped around the injured limb of the victim. As illustrated in FIG. 1, the straps 16 of the preferred embodiment of the medical device 10 shown in FIGS. 1–3 are wrapped around the arm A of the victim. The open ends of the sleeve 12 are closed and the sleeve 12 is positioned and secured on the arm A of the victim by tucking the free ends of the straps 16 under the portions of the straps 16 wrapped around the arm A of the victim. The straps 16 may instead be wrapped around the sleeve 12 to apply pressure to the wound as previously described and secured in the same manner. Alternatively, medical tape may be placed over the free ends of the wrapped straps 16 to close the open ends of the sleeve 12 and to secure the medical device 10 in position over the wound. The straps 16 may also include hook and loop fasteners, snaps, metal clips or any other conventional means for securing the free ends of the straps 16. The straps 16 are preferably made of an absorbent material, such as the material commonly used in the manufacture of diapers and sanitary napkins, that prevents the passage of liquids, such as water, oil and fuel, from the surrounding environment to the wound through the straps 16 of the medical device 10. At the same time, the material of the straps 16 prevents the passage of blood and other body fluids from the wound to the surrounding environment through the straps 16 of the medical device 10.

As best shown in FIG. 3, the material of the sleeve 12 of the medical device 10 comprises at least two, and preferably three, layers. The material of the sleeve 12 comprises a middle layer 22 and an outer layer 24 positioned outwardly of the middle layer 22. The material of the sleeve 12 may further comprise an optional inner layer 20 positioned inwardly of the middle layer 22. The middle layer 22 is made of an absorbent material, such as cotton or dried wood pulp, that is suitable for absorbing the blood and other body fluids of the victim. The outer layer 24 is made of a non-absorbent, non-porous material, such as polyethylene or polypropylene, that does not permit blood and other body fluids absorbed by the middle layer 22 to pass through the outer layer 24 to the environment surrounding the medical device 10. The outer layer 24 is also substantially transparent. Accordingly, rescue and medical personnel can observe the extent of the continued bleeding of the wound without removing the medical device 10, and thereby potentially exposing the wound to further injury or the environment or exposing themselves to the blood and other body fluids of the victim.

If utilized, the optional inner layer 20 is made of a non-adherent, porous material, such as a fine organic fabric or plastic mesh, that is commonly used in the manufacture of adhesive strip bandages, diapers and sanitary napkins. Thus, the inner layer 20 (which is positioned adjacent the wounded area or the dressing) permits the absorbent middle layer 22 to wick blood and other body fluids away from the wound to the middle layer 22 where the extent of the continued bleeding may be observed through the transparent outer layer 24. At the same time, the non-adherent inner layer 20 prevents the medical device 10 from sticking to the wounded area or the dressing so that removal of the medical device 10 does not cause the wound to reopen and begin to bleed profusely. Accordingly, rescue and medical personnel can observe the extent of the continued bleeding of the wound without removing the medical device 10, and thereby potentially exposing the wound to infection or further injury or dislodging a blood clot that has formed over the wound. The non-adherent, porous material of the inner layer 20 may also be impregnated with an antibacterial agent to prevent infection of the wound.

As described and illustrated herein, the preferred embodiment of the medical device 10 shown in FIGS. 1–3 is open at both ends so that the medical device 10 may be easily positioned and secured over a victim's arm or leg to completely surround the wounded area or the dressing covering the wound. The sleeve 12 of the medical device 10 can be provided in different sizes, and in particular in different lengths and diameters, to fit any size arm or leg. The open ends of the sleeve 12 are closed and the medical device 10 is secured in position over the wounded area or the dressing by wrapping the straps 16 around the limb of the victim or the sleeve 12 and securing the free ends of the straps 16 to the underlying portions of the straps 16 in the manner previously described. Once the free ends of the straps 16 are secured, the medical device 10 covers the wounded area or the dressing and completely contains blood and other body fluids within the medical device 10. Thus, the wound is protected from further injury and the environment while rescue and medical personnel are protected from exposure to the blood and other body fluids of the victim. Once the victim is stabilized and recovering in a medical facility, the medical device 10 prevents the blood and other body fluids excreted from the wound during the healing process from coming into contact with the surrounding environment, such as bedding, clothing and furniture.

Figure 6:
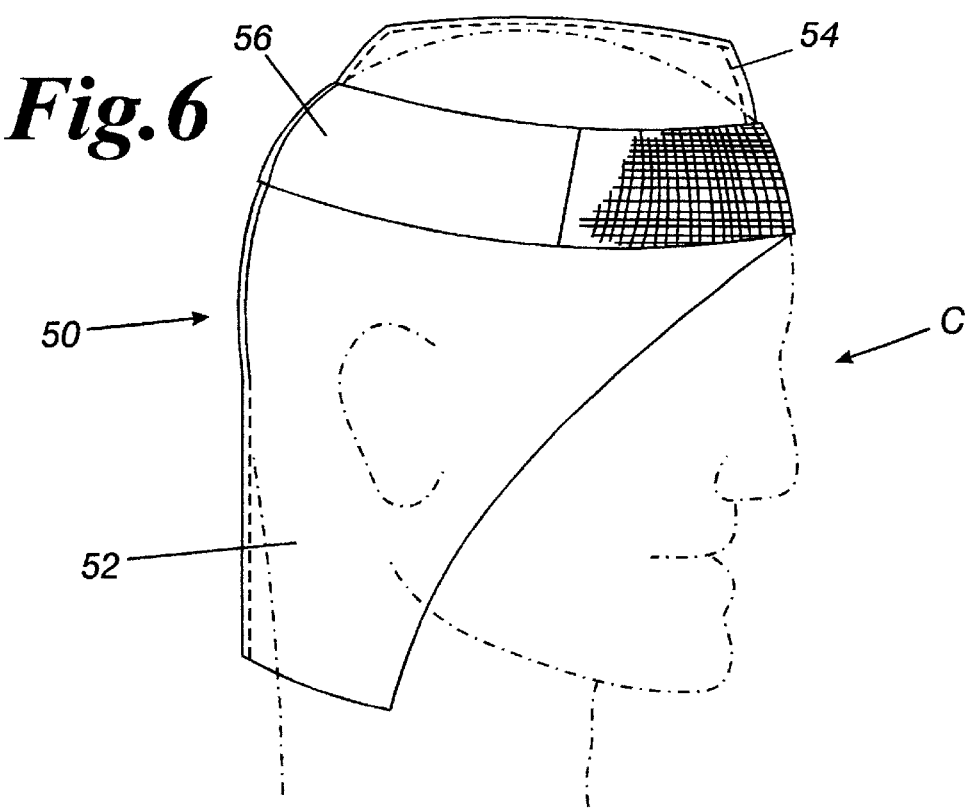
FIG. 6 is a side elevation view of an alternative preferred embodiment of a medical device according to the invention secured and positioned over a wounded area or a dressing on the head of a victim, with the head of the victim depicted by phantom lines.

Alternative preferred embodiments of a medical device 30, 40, 50 according to the invention are shown in FIGS. 4–6, respectively. Each of the alternative preferred embodiments of the medical device 30, 40, 50 shown in FIGS. 4–6 comprises a sleeve 32, 42, 52 having one open end and one closed end. Thus, the medical device 30, 40, 50 can be easily positioned and secured over a wounded area or a dressing on an appendage, and in particular, over a wound on a hand, foot or head. The medical device 30, 40, 50 may be manufactured in different predetermined sizes to fit over appendages of various sizes. The sleeve 32, 42, 52 of the medical devices 30, 40, 50 is made of the same material as the sleeve 12 of the medical device 10 and likewise comprises at least two layers, and preferably three layers, as previously described. The medical device 30, 40, 50 further comprises at least one closure strap 36, 46, 56 as will be described hereinafter. Preferably, the at least one strap 36, 46, 56 is made of the same material as the strap 16 of the medical device 10.

FIG. 4 illustrates the medical device 30 properly positioned and secured over a wounded area or a dressing on the hand H of a victim. A seam 34, formed as previously described, extends along the length of the sleeve 32 and the closed end. The seam 34 is sealed as previously described and thereby prevents the passage of liquids, such as water, oil or fuel, from the surrounding environment to the wound through the seam 34 of the medical device 30. At the same time, the seam 34 prevents the passage of blood and other body fluids from the wound to the surrounding environment through the seam 34 of the medical device 30. The open end of the sleeve 32 is cut at an angle to permit the medical device 30 to be positioned over the fingers of the hand H while leaving the wrist and thumb of the hand H exposed. The medical device 30 is positioned over the hand H of the victim and secured in place by wrapping the strap 36 around the wrist and between the thumb and index finger of the hand H, or by wrapping the strap 36 around the sleeve 32 of the medical device 30, in the manner previously described.

FIG. 5 illustrates the medical device 40 properly positioned and secured over a wounded area or a dressing on the foot F of a victim. Like the alternative preferred embodiment of the medical device 30 illustrated in FIG. 4, the medical device 40 has one open end and one closed end. A seam 44, formed as previously described, extends along the sleeve 42 and the closed end. The seam 44 is sealed as previously described and thereby prevents the passage of liquids, such as water, oil or fuel, from the surrounding environment to the wound through the seam 44 of the medical device 40. At the same time, the seam 44 prevents the passage of blood and other body fluids from the wound to the surrounding environment through the seam 44 of the medical device 40. The open end of the sleeve 42 is cut at an angle to permit the medical device 40 to be positioned over the toes of the foot F while leaving the ankle of the foot F exposed. The medical device 40 is positioned over the foot F of the victim and secured in place by wrapping the strap 46 around the ankle, or by wrapping the strap 46 around the sleeve 42 of the medical device 40, in the manner previously described. The medical device 40 may also be manufactured in the form of a sock having a heel portion. However, for ease of manufacture and use, the medical device 40 is formed as shown in FIG. 5 with an angled cut formed in the open end of the sleeve 42. This method of manufacture requires less material and effort while permitting the medical device 40 to be used on feet of various sizes.

Figure 7:
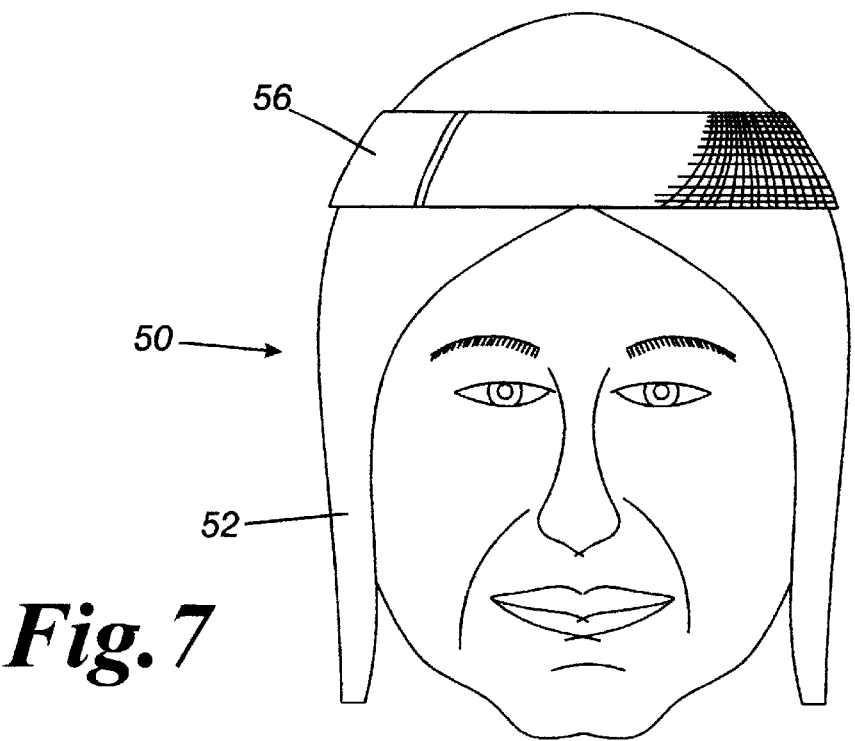
FIG. 7 is a front elevation view of the medical device of FIG. 6.

FIGS. 6 and 7 illustrate the medical device 50 properly positioned and secured over a wounded area or a dressing on the head C of a victim. Like the alternative preferred embodiments of the medical device 30, 40 illustrated in FIGS. 4 and 5, the medical device 50 has one open end and one closed end. A seam 54, formed as previously described, extends along the sleeve 52 and the closed end. The seam 54 is sealed as previously described and thereby prevents the passage of liquids, such as water, oil or fuel, from the surrounding environment to the wound through the seam 54 of the medical device 50. At the same time, the seam 54 prevents the passage of blood and other body fluids from the wound to the surrounding environment through the seam 54 of the medical device 50. The open end of the sleeve 52 is cut at an angle to permit the medical device 50 to be positioned over the head C of the victim while leaving the face and neck of the victim exposed. The medical device 50 is positioned over the head C of the victim and secured in place by wrapping the strap 56 around the sleeve 52 of the medical device 50 on the head C of the victim in the manner previously described.

In each of the embodiments of the medical device 30, 40, 50 shown in FIGS. 4–6, the corresponding seam 34, 44, 54 forms the closed end and further forms a closed side that extends along the seam 34, 44, 54 from the open end. At the same time, the seam 34, 44, 54 defines an open side opposite the closed side that extends from the closed end and the closed side. Thus, the closed end, open end, closed side and open side define a cavity within the sleeve 32, 42, 52 for the hand H, foot F or head C of the victim. The closed side functions as the portion of the sleeve 32, 42, 52 that receives and supports the wounded area or the dressing on the hand H, foot F or head C of the victim. The open side functions as the portion of the sleeve 32, 42, 52 through which the wounded area or the dressing on the hand H, foot F or head C of the victim is inserted into the sleeve 32, 42, 52. As previously described, the sleeve 32, 42, 52 may further comprise an angled portion along the open end and the open side to facilitate inaction of the hand H, foot F or head C of the victim into the cavity.

While certain representative embodiments and details have been shown for purposes of illustrating the invention, it will be apparent to those skilled in the art that various changes in the form and detail of the invention may be made without departing from the spirit and scope of the invention as defined by the appended claims.

What is claimed is:

1. A medical device for containing body fluids comprising:
   a sleeve defining a longitudinal axis and having one open end and one closed end, said sleeve made of a protective material comprising an absorbent layer, a substantially transparent, nonporous layer positioned outwardly of said absorbent layer and a non-adherent, porous layer positioned inwardly of said absorbent layer; and
   a strap attached to said sleeve for closing the open end to thereby position and secure said sleeve over a wounded area or over a dressing covering a wound.

2. A medical device according to claim 1 wherein said sleeve is cut at an angle relative to the longitudinal axis defined by said sleeve to form the open end.

3. A medical device according to claim 2 wherein said sleeve is configured to at least partially cover the hand, foot or head of a human being.

4. A medical device for containing body fluids comprising:
   a sleeve made of a protective material, said sleeve defining a longitudinal axis and having a closed end, an open end opposite the closed end, and at least one closed side defining a cavity therein; and
   a strap having a first end attached to said sleeve for closing the open end and thereby secure said sleeve over a wounded area of a human being or over a dressing covering a wounded area of a human being within the cavity;
   wherein the protective material comprises an absorbent layer, a substantially transparent, nonporous layer positioned outwardly of said absorbent layer and a non-adherent, porous layer positioned inwardly of said absorbent layer.

5. A medical device according to claim 4, wherein said sleeve further comprises an open side opposite the closed side.

6. A medical device according to claim 4 wherein the closed end and the closed side of said sleeve are closed by a seam extending at least along the closed end and the closed side.

7. A medical device according to claim 4 wherein said sleeve further comprises an open side opposite the closed side and wherein said sleeve comprises an angled portion extending between the open end and the open side to facilitate insertion of the wounded area of the human being into the cavity.

8. A medical device according to claim 4 wherein said sleeve is sized and shaped to receive the hand of a human being within the cavity.

9. A medical device according to claim 4 wherein said sleeve is sized and shaped to receive the foot of a human being within the cavity.

10. A medical device according to claim 4 wherein said sleeve is sized and shaped to receive the head of a human being within the cavity.

11. A medical device for containing body fluids comprising:

- a sleeve made of a protective material comprising an absorbent layer, a substantially transparent, nonporous layer positioned outwardly of said absorbent layer and a non-adherent, porous layer positioned inwardly of said absorbent layer, said sleeve defining a longitudinal axis and having a closed end, an open end opposite the closed end, a closed side and an open side opposite the closed side, the closed end and the closed side being formed by a seam, the closed end, open end, closed side and open side defining a cavity within said sleeve, said sleeve further comprising an angled portion extending between the open end and the open side to facilitate insertion of a hand, foot or head of a human being within the cavity; and
- a strap having a first end attached to said sleeve for closing the open end and thereby secure said sleeve over a wounded area on the hand, foot or head of the human being or over a dressing covering a wounded area of the hand, foot or head of the human being.

* * * * *